(12) United States Patent
Kim et al.

(10) Patent No.: US 10,786,622 B2
(45) Date of Patent: *Sep. 29, 2020

(54) LIQUID MEDICATION INJECTION DEVICE

(71) Applicant: EOFLOW CO., LTD., Seongnam-si, Gyeonggi-do (KR)

(72) Inventors: Seung Ha Kim, Goyang-si (KR); Jesse Jaejin Kim, Seongnam-si (KR)

(73) Assignee: EOFlow Co., Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/080,652

(22) PCT Filed: Feb. 24, 2017

(86) PCT No.: PCT/KR2017/002071
§ 371 (c)(1),
(2) Date: Aug. 28, 2018

(87) PCT Pub. No.: WO2017/150850
PCT Pub. Date: Sep. 8, 2017

(65) Prior Publication Data
US 2019/0015586 A1    Jan. 17, 2019

(30) Foreign Application Priority Data

Feb. 29, 2016 (KR) .................. 10-2016-0024676

(51) Int. Cl.
*A61M 5/158* (2006.01)
*A61M 5/32* (2006.01)
(Continued)

(52) U.S. Cl.
CPC ............ *A61M 5/158* (2013.01); *A61M 5/142* (2013.01); *A61M 5/2033* (2013.01); *A61M 5/3287* (2013.01); *A61M 2005/1585* (2013.01)

(58) Field of Classification Search
CPC ................ A61M 5/158; A61M 5/2033; A61M 2005/1585; A61M 2005/3022;
(Continued)

(56) References Cited

U.S. PATENT DOCUMENTS 3,572,336 A    3/1971  Hershberg
7,238,192 B2   7/2007  List et al.
(Continued)

FOREIGN PATENT DOCUMENTS

JP    3993529        10/2007
JP    2012-115672 A   6/2012
(Continued)

OTHER PUBLICATIONS

International Search Report dated May 30, 2017 in PCT Application No. PCT/KR2017/002071; 3 pages.
(Continued)

*Primary Examiner* — Brandy S Lee
*Assistant Examiner* — Nidah M Hussain
(74) *Attorney, Agent, or Firm* — Knobbe, Martens, Olson & Bear, LLP

(57) ABSTRACT

Provided is a liquid medicine injection device having a needle holder slid immediately by using the elasticity of a spring such that a needle installed at the needle holder may be instantly inserted into a patient.

8 Claims, 13 Drawing Sheets

(51) Int. Cl.
*A61M 5/20* (2006.01)
*A61M 5/142* (2006.01)

(58) Field of Classification Search
CPC .......... A61M 5/14244; A61M 5/14248; A61M 5/14252; A61M 2005/14252
USPC .................................................. 604/136, 117
See application file for complete search history.

(56) References Cited

U.S. PATENT DOCUMENTS

| | | | |
|---|---|---|---|
| 9,522,229 B2* | 12/2016 | Sonderegger | A61M 5/3287 |
| 2003/0216767 A1* | 11/2003 | List | A61B 5/150412 |
| | | | 606/181 |
| 2014/0058353 A1* | 2/2014 | Politis | A61M 5/14248 |
| | | | 604/506 |
| 2016/0089056 A1* | 3/2016 | Limaye | A61M 5/46 |
| | | | 600/365 |

FOREIGN PATENT DOCUMENTS

| | | |
|---|---|---|
| JP | 2013-504403 | 2/2013 |
| JP | 2014-510571 | 5/2014 |
| JP | 2015-037552 A | 2/2015 |
| KR | 10-2004-0039278 | 5/2004 |
| KR | 10-2009-0109581 | 10/2009 |
| WO | WO 2012/134588 A1 | 10/2012 |

OTHER PUBLICATIONS

Extended European Search Report dated Sep. 23, 2019 in European Application No. 17760254.7; 6 pages.
Office Action dated Jan. 10, 2017 in Korean Patent Application No. 10-2016-0024676; 11 pages.

* cited by examiner

LIQUID MEDICATION INJECTION DEVICE

TECHNICAL FIELD

The present disclosure relates to liquid medicine injection devices.

BACKGROUND ART

Liquid medicine injection devices such as insulin injection devices are used to inject liquid medicines into the bodies of patients, which are used by professional medical staff such as nurses or doctors but are mostly used by ordinary persons such as caretakers or patients themselves. Since the liquid medicines injected through the liquid medicine injection devices are often required to be taken by the patients for a long period of time, the patients may suffer the pain of the needles of the liquid medicine injection devices being inserted many times.

A liquid medicine injection device has a needle for discharging liquid medicine, and the needle should be inserted into the body of the patient, and in this process, the patient may inevitably suffer the pain due to the insertion of the needle. In addition, the pain due to the insertion of the needle may cause the patient to have fear of the liquid medicine injection device and thus the objection to the liquid medicine injection device.

Provided is a liquid medicine injection device that may minimize the pain and fear due to the insertion of a needle.

SOLUTION TO PROBLEM

According to an aspect of the present disclosure, a liquid medicine injection device includes: a casing: a button exposed outside the casing; a needle holder located in the casing and coupled to a needle; a spring located in the casing and interposed between the button and the needle holder; and a guiding member located in the casing to support the needle holder.

The needle holder may be provided to rotate by an operation of the button, and the needle holder may include: a first support supported by the guiding member in a first state; and a guiding groove provided to be adjacent to the first support and to pass the guiding member therethrough in a second state where the needle holder is rotated from the first state.

The first support may include: a support groove formed at a surface facing an insertion direction of the needle and connected to the guiding groove; and a support stopper located between the support groove and the guiding groove to provide a resistance to the rotation of the needle holder.

The guiding member may include a second support provided to support the first support in the first state.

The second support may include a first support portion located downstream with respect to a rotation direction of the needle holder and a second support portion located upstream with respect to the rotation direction of the needle holder, and the first support portion may be located more adjacent to the button than the second support portion.

The button may be provided to slide in a direction facing the needle holder, and the liquid medicine injection device may further include a stopper located adjacent to the guiding member and provided to control the sliding of the button.

The button may include a first coupling portion protruding toward the needle holder, and the needle holder may include a second coupling portion provided to couple to the first coupling portion.

According to another aspect of the present disclosure, a liquid medicine injection device includes: a casing including a base: a button exposed outside the casing; a needle holder located in the casing; and a spring located in the casing and interposed between the button and the needle holder, wherein the needle holder is provided to be located spaced apart from the base of the casing in a first state, and the needle holder is provided to be driven toward the base by the elasticity of the spring while being transformed into a second state where the needle holder is rotated from the first state.

The liquid medicine injection device may further include a guiding member provided to support the needle holder to be spaced apart from the base in the first state and to guide the needle holder in the second state.

The needle holder may include: a first support supported by the guiding member in the first state; and a guiding groove provided to be adjacent to the first support and to pass the guiding member therethrough in the second state where the needle holder is rotated from the first state.

The guiding member may include a second support provided to support the first support in the first state.

ADVANTAGEOUS EFFECTS OF DISCLOSURE

According to the embodiments of the present disclosure described above, since the needle holder may be immediately slid by using the elasticity of the spring, the needle installed at the needle holder may be instantly inserted into the patient.

Due to the instant insertion of the needle, the pain of the patient may be minimized and the patient's fear for the needle may be reduced.

Accordingly, the objection to the liquid medicine injection device by the patient having to be provided with the liquid medicine for a long period of time may be reduced, and the liquid medicine may be smoothly injected into the patient, thus contributing to the health and/or treatment of the patient.

DETAILED DESCRIPTION OF CERTAIN ILLUSTRATIVE EMBODIMENTS

Figure 1:
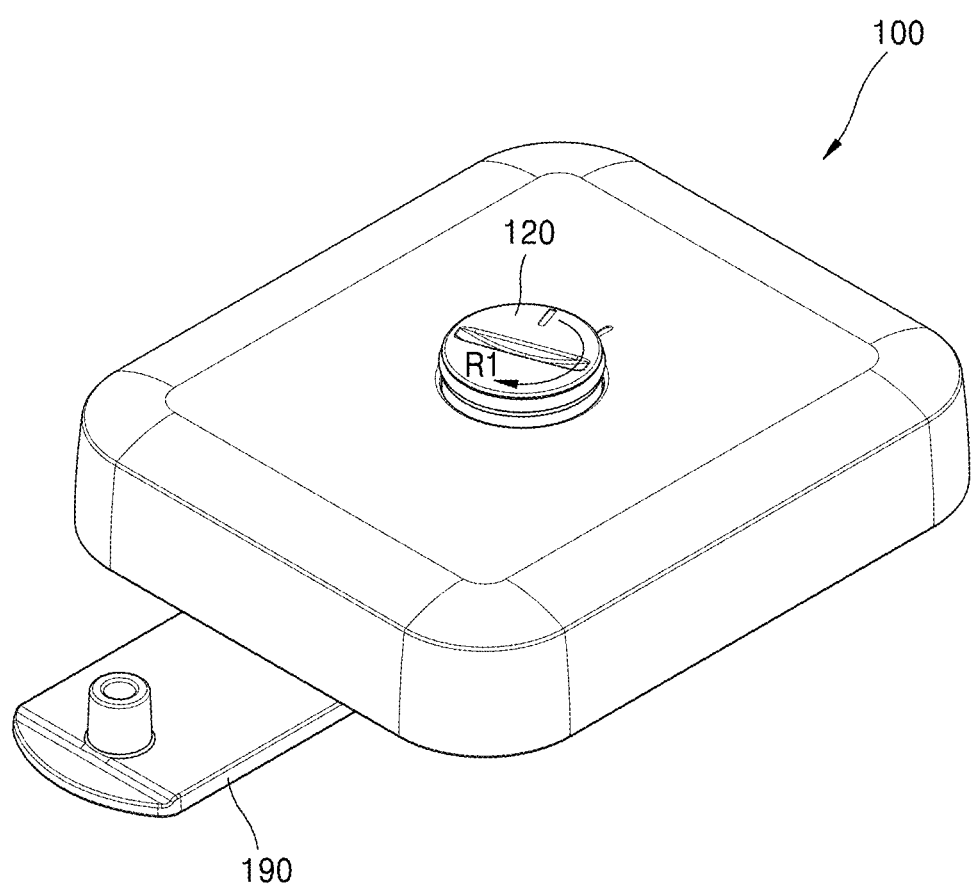
FIG. 1 is a perspective view of a liquid medicine injection device according to an embodiment.

The present disclosure may include various embodiments and modifications, and certain embodiments thereof are illustrated in the drawings and will be described herein in detail. The effects and features of the present disclosure and the accomplishing methods thereof will become apparent from the following description of the embodiments taken in conjunction with the accompanying drawings. However, the present disclosure is not limited to the embodiments described below, and may be embodied in various modes.

Hereinafter, embodiments of the present disclosure will be described in detail with reference to the accompanying drawings. In the following description, like reference numerals will denote like elements, and redundant descriptions thereof will be omitted.

As used herein, the singular forms "a", "an", and "the" are intended to include the plural forms as well, unless the context clearly indicates otherwise.

It will be understood that the terms "comprise", "include", and "have" used herein specify the presence of stated features or components, but do not preclude the presence or addition of one or more other features or components.

It will be understood that when a layer, region, or component is referred to as being "formed on" another layer, region, or component, it may be directly or indirectly formed on the other layer, region, or component. That is, for example, intervening layers, regions, or components may be present.

When a certain embodiment may be implemented differently, a particular process order may be performed differently from the described order. For example, two consecutively described processes may be performed substantially at the same time or performed in an order opposite to the described order.

Sizes of components in the drawings may be exaggerated for convenience of description. In other words, since sizes and thicknesses of components in the drawings are arbitrarily illustrated for convenience of description, the following embodiments are not limited thereto.

FIG. 1 is a perspective view of a liquid medicine injection device according to an embodiment.

A liquid medicine injection device 100 according to an embodiment may include a button 120 exposed at one side thereof and a needle cover assembly 190 provided at the other side thereof.

The button 120 may be provided and exposed to a user such that the button 120 may be pressed and/or rotated by the user. The needle cover assembly 190 may be provided to protect a needle and may be separated when the user uses the liquid medicine injection device 100.

Figure 2:
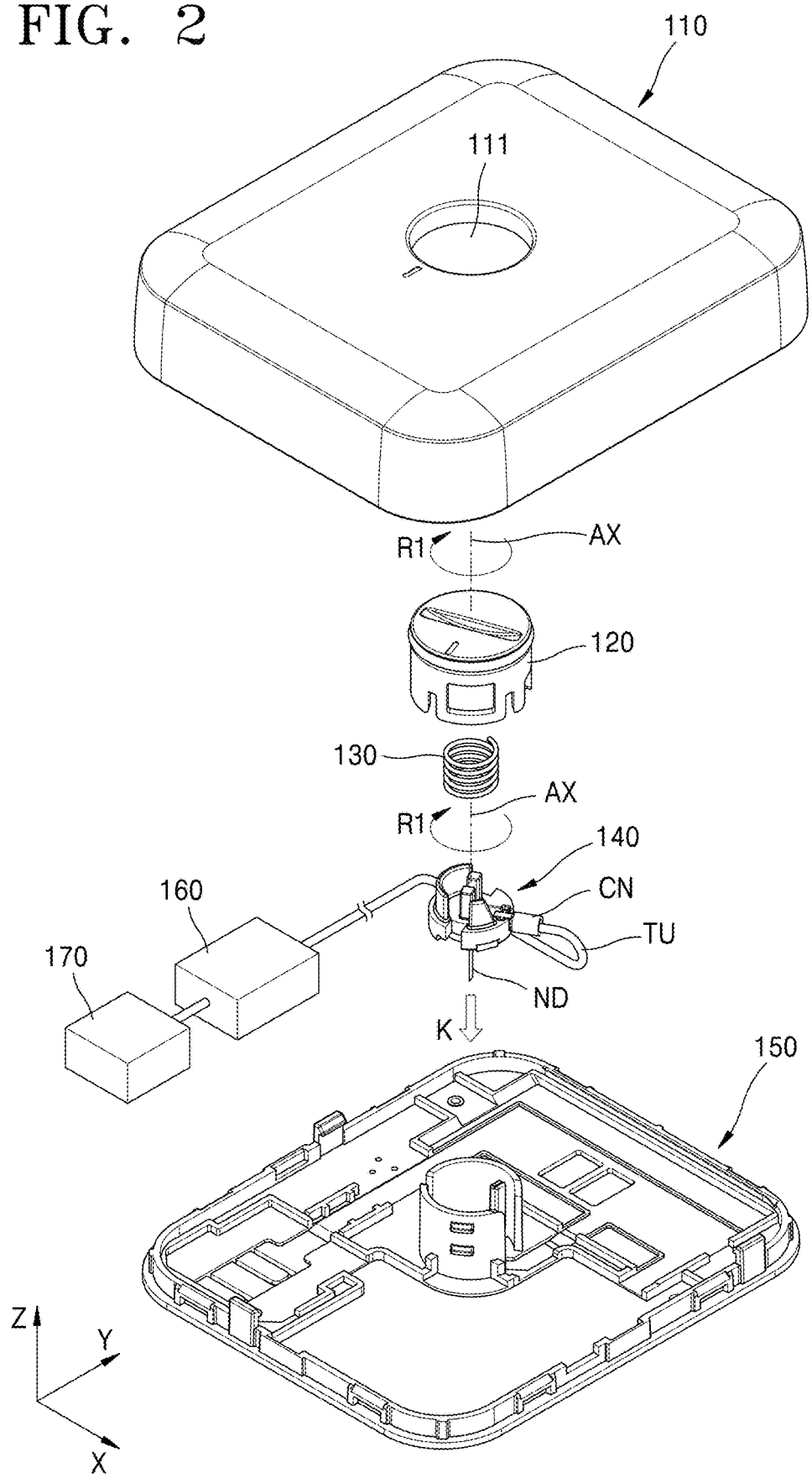
FIG. 2 is an exploded perspective view of the liquid medicine injection device illustrated in FIG. 1.

The above-described liquid medicine injection device may be more particularly configured as illustrated in FIG. 2.

A liquid medicine injection device according to an embodiment may include a casing, and the casing may include a first casing 110 and a second casing 150 coupled to each other.

The first casing 110 may be exposed to the user even after the liquid medicine injection device is installed at the body of the user, and an opening 111 may be formed at a portion of the first casing 110. The button 120 may pass through the opening 111, and the button 120 may be exposed to the user.

The button 120, a spring 130, a needle holder 140, a pump 160, and a liquid medicine storage unit 170 may be located between the first casing 110 and the second casing 150 coupled to each other, that is, inside the casing.

Although not illustrated, the liquid medicine storage unit 170 may include a storage tank for storing liquid medicine and a piston for discharging the liquid medicine; however, the present disclosure is not limited thereto and the liquid medicine storage unit 170 may include only the storage tank. The liquid medicine may be a liquid including medicine such as insulin.

The liquid medicine storage unit 170 may be connected to the pump 160 through a liquid connection member such as a tube. The pump 160 may be configured to pump the liquid medicine toward the needle holder 140 and may pump a certain amount of liquid medicine according to a pumping cycle. The pump 160 may be electrically connected to a separate power supply and a controller (not illustrated) to suck the liquid medicine from the liquid medicine storage unit 170 and discharge the sucked liquid medicine to the needle holder 140.

The pump 160 may include any types of pumps having a liquid medicine suction force and a liquid medicine discharge force by electricity. For example, the pump 160 may include any types of pumps such as a mechanical displacement type micropump and an electromagnetic motion type micropump. The mechanical displacement type micropump may be a pump that uses solid or fluid motion such as a gear or diaphragm to generate a pressure difference to induce fluid flow, examples of which may include a diaphragm displacement pump, a fluid displacement pump, and a rotary pump. The electromagnetic motion type micropump may be a pump that uses electric or magnetic energy for fluid movement, examples of which may include an electro-hydrodynamic pump (EHD), an electro-osmotic pump, a magneto-hydrodynamic pump, and an electro-wetting pump.

The pump 160 may be connected to the needle holder 140 through a tube TU and a connector CN. The tube TU connected to the pump 160 may be connected to the connector CN and it may be connected to a needle ND while being supported by the needle holder 140. Thus, the liquid medicine discharged from the pump 160 may be discharged through the needle ND through the tube TU and the connector CN. For this purpose, the needle holder 140 may be coupled to the needle ND.

The needle holder 140 may be arranged to face the button 120, and the spring 130 may be interposed between the needle holder 140 and the button 120. The button 120, the spring 130, and the needle holder 140 may be arranged along an axis AX. The axis AX may be parallel to a Z axis in the drawings.

In the embodiment illustrated in FIG. 2, the liquid medicine storage unit 170 and the pump 160 are schematically illustrated and are not limited to the illustrated shapes and/or arrangements.

Figure 3:
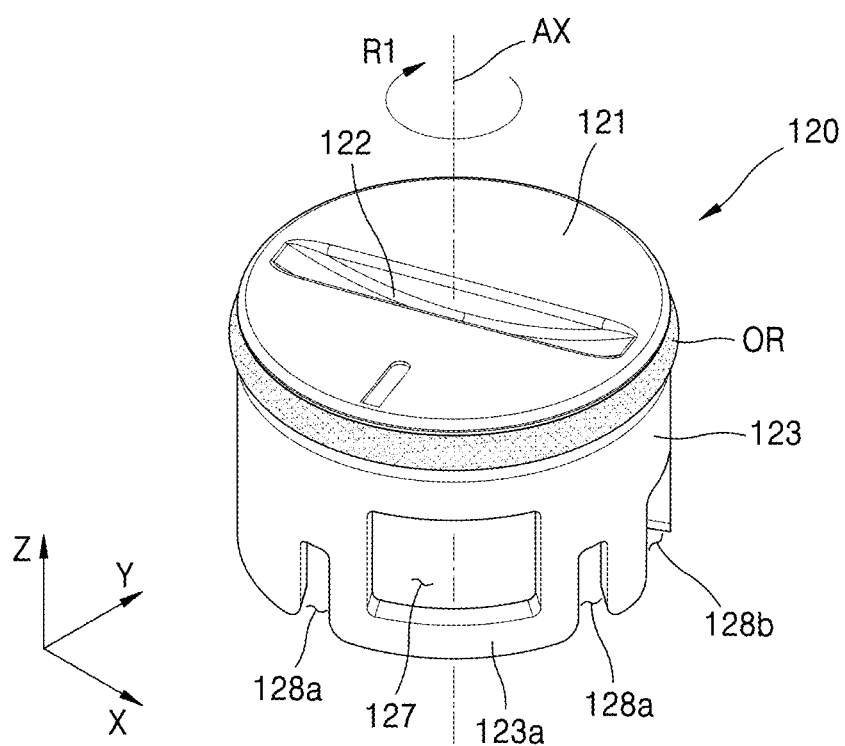
FIG. 3 is a perspective view of a button according to an embodiment.
Figure 4:
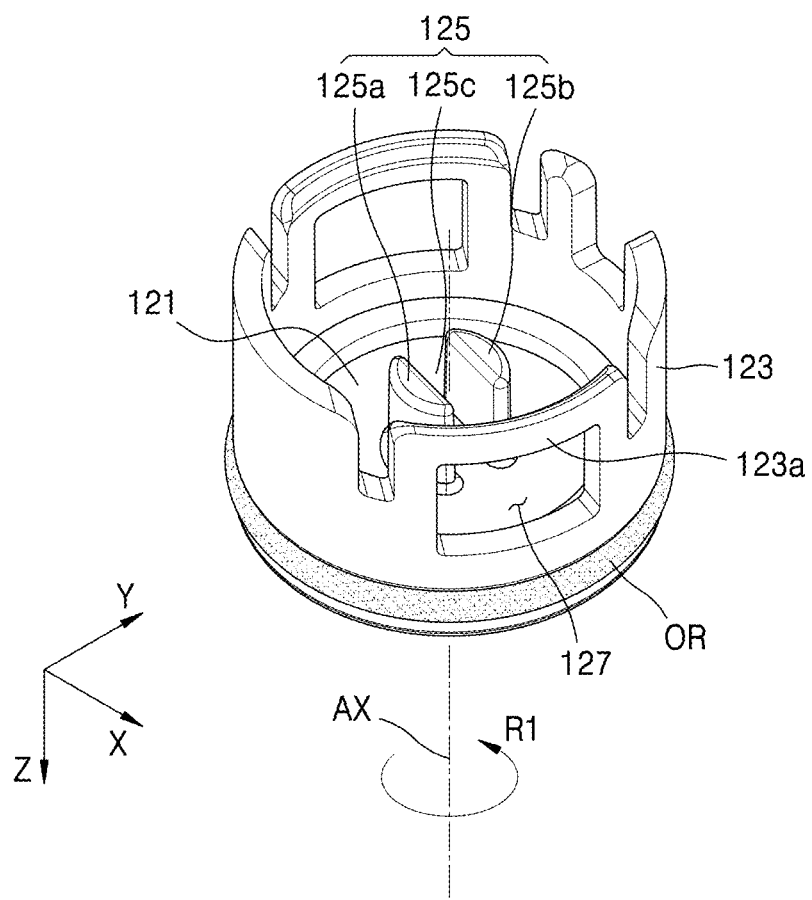
FIG. 4 is a bottom perspective view of the button illustrated in FIG. 3.

FIGS. 3 and 4 are respectively a perspective view and a bottom perspective view of the button 120 according to an embodiment.

The button 120 may be formed in a substantially cylindrical shape and may be provided to rotate on the axis AX along a rotation direction R1. A rotation groove 122 may be formed at a surface 121 of the button 120 in a Z-axis direction such that the user may easily rotate the button 120. The user may easily rotate the button 120 by inserting a nail or a coin into the rotation groove 122.

The button 120 may have a cylindrical side surface 123, and a ring member OR may be inserted near the top of the side surface 123. An O-ring may be used as the ring member OR to prevent the liquid medicine from leaking between the button 120 and the opening 111 of the first casing 110. Alternatively, the ring member OR may provide a certain resistance to the pressure when the button 120 is pressed by the user and/or prevent the button 120 from protruding easily after being pressed.

As illustrated in FIGS. 3 and 4, a fastening opening 127 may be formed at the side surface 123. At least one pair of fastening openings 127 may be provided at mutually symmetrical portions of the side surface 123. The fastening opening 127 may be located at a substantially central portion of the side surface 123 in the Z-axis direction, and thus, a fastening rod 123a may be formed at an edge of the fastening opening 127. The fastening opening 127 may be fastened to a stopper (which will be described below), and in this case, the fastening rod 123a may be caught by the stopper to prevent the button 120 from being detached. The fastening opening 127 may be formed to extend in an X-Y plane direction along an outer circumferential surface of the side surface 123 such that the button 120 may rotate along the rotation direction R1 while being fastened to the stopper.

A first groove 128a may be formed at a portion of the side surface 123 adjacent to the fastening opening 127. The first groove 128a may be located on both sides of each fastening opening 127 to provide a certain elasticity when the fastening opening 127 is fastened to the stopper.

A second groove 128b may be further formed at the side surface 123, and when the button 120 is coupled to the needle holder 140, the connector CN may penetrate the side surface 123 through the second groove 128b.

As illustrated in FIG. 4, a first coupling portion 125 may be provided at an inner surface of the button 120, for example, at a surface facing the needle holder 140. The first coupling portion 125 may be coupled to a second coupling portion of the needle holder 140 (which will be described below). The first coupling portion 125 may include a first coupling protrusion 125a and a second coupling protrusion 125b that protrude toward the needle holder 140 and face each other while being spaced apart from each other, and a gap 125c may be provided between the first coupling protrusion 125a and the second coupling protrusion 125b. The first coupling portion 125 may not be fixedly fastened to the second coupling portion (which will be described below and may be any type that may engage with the second coupling portion when the user presses the button 120 and may transmit the rotational force of the button 120 to the needle holder 140 when the user rotates the button 120.

Figure 5:
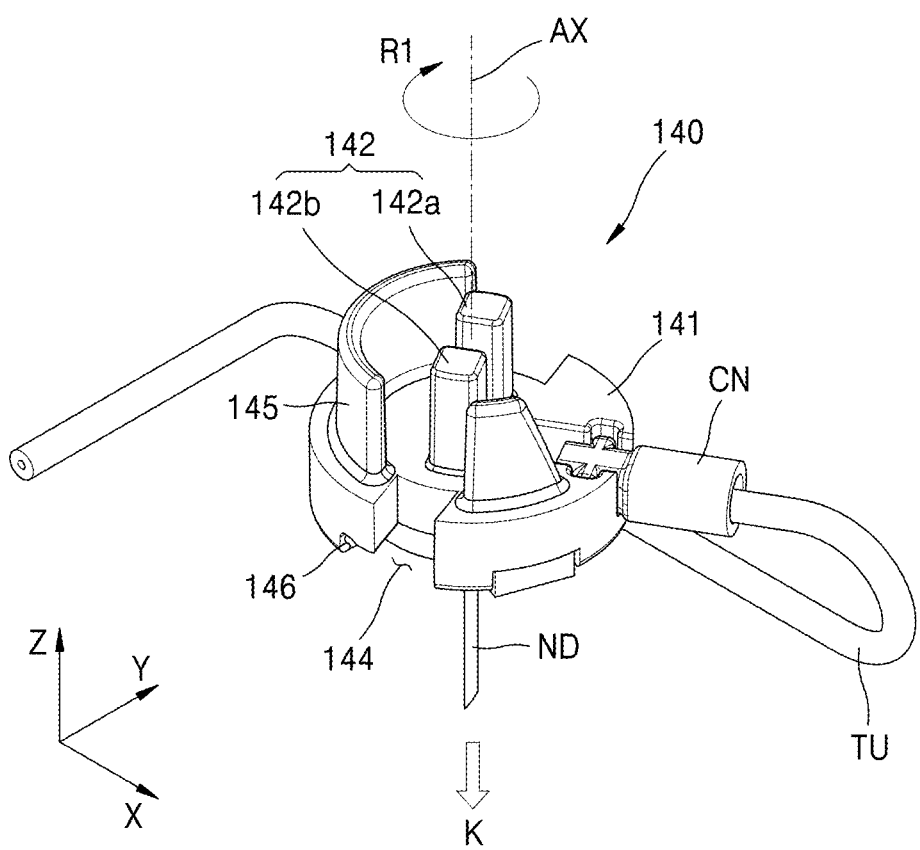
FIG. 5 is a perspective view of a needle holder according to an embodiment.
Figure 6:
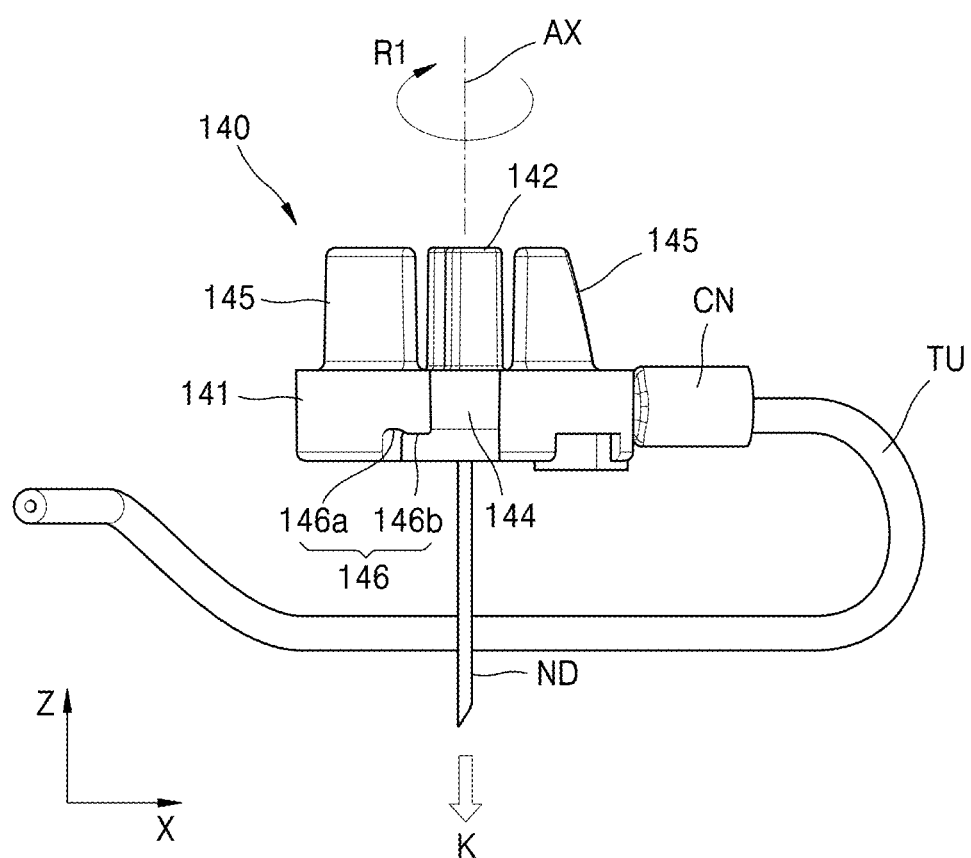
FIG. 6 is a side view of the needle holder illustrated in FIG. 5.
Figure 7:
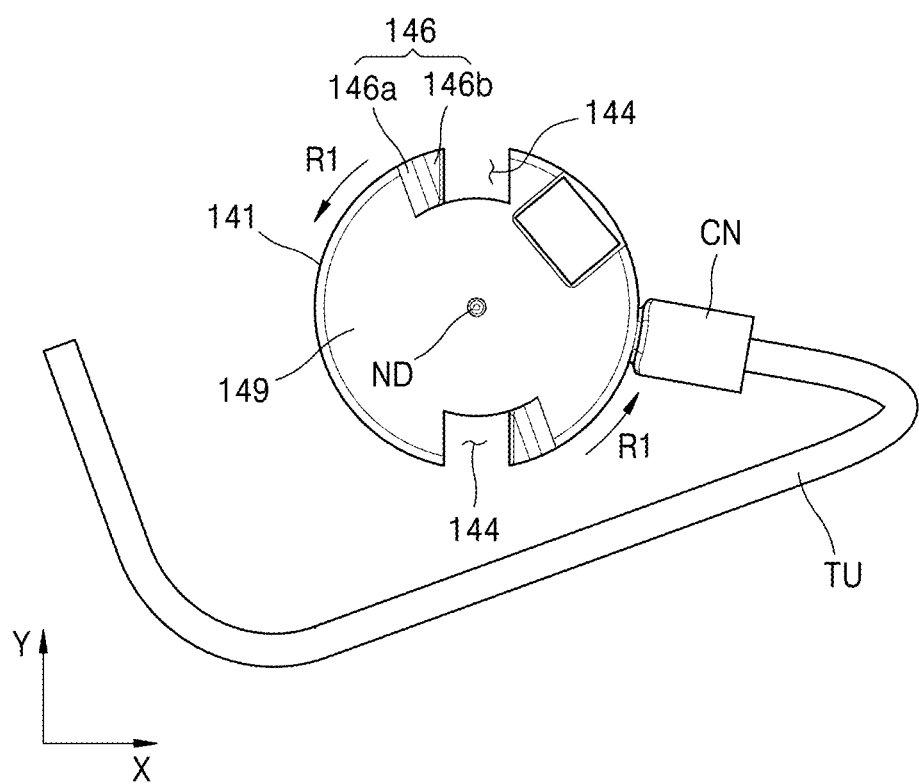
FIG. 7 is a bottom view of the needle holder illustrated in FIG. 5.

FIGS. 5 to 7 are respectively a perspective view, a side view, and a bottom view of the needle holder 140 according to an embodiment.

The needle holder 140 according to an embodiment may have a substantially disk-shaped body 141 to rotate easily along the rotation direction R1. As described above, the connector CN connected to the pump 160 may be coupled to the body 141.

The needle ND may be coupled to the body 141 in a direction opposite to the button 120, and the needle ND may be connected to the connector CN to communicate with the tube TU. As illustrated in FIG. 7, the needle ND may be located at the center of a bottom surface 149 of the body 141.

On the opposite side of a portion of the body 141 coupled to the connector CN, a support 145 may be erected in the Z-axis direction. The support 145 may be formed in a circumferential direction along an edge of the body 141. The support 145 may prevent the needle holder 140 from being tilted to one side by the tension of the tube TU and may guide the needle holder 140 to move linearly along an insertion direction K of the needle ND.

A second coupling portion 142 may be provided at a surface of the body 141 facing the button 120.

The second coupling portion 142 may be coupled to the first coupling portion 125. The second coupling portion 142 may include a first coupling protrusion 142a and a second coupling protrusion 142b that protrude toward the button 120 while being spaced apart from each other. The first coupling protrusion 142a and the second coupling protrusion 142b may be any type that may engage with the first coupling portion 125 when the user presses the button 120 and may transmit the rotational force of the button 120 to the needle holder 140 when the user rotates the button 120, For example, when the first coupling portion 125 and the second coupling portion 142 are coupled to each other, the gap 125c between the first coupling protrusion 125a and the second coupling protrusion 125b of the first coupling portion 125 may be inserted between the first coupling protrusion 142a and the second coupling protrusion 142b of the second coupling portion 142. Accordingly, the first coupling portion 125 and the second coupling portion 142 may be engaged with each other.

The first coupling portion 125 may be inserted into one end of the spring 130 illustrated in FIG. 2 and the second coupling portion 142 may be inserted into the other end of the spring 130, so that the spring 130 may be fixed between the button 120 and the needle holder 140. The spring 130 may be coupled between the button 120 and the needle holder 140 in a compressed state to some degree; however, the present disclosure is not limited thereto and the spring 130 may be interposed between the button 120 and the needle holder 140 in a normal state that is an uncompressed state in a state where the user does not press the button 120.

The needle holder 140 may include a first support 146 and a guiding groove 144.

The first support 146 may be supported by a guiding member 155 (see FIG. 8) (which will be described below) in a first state before the needle holder 140 rotates and may be located spaced apart from a base 151 of the second casing 150 by a certain distance. That is, in the first state, the needle holder 140 may float to some degree from the base 151 in the Z-axis direction.

The guiding groove 144 may be located adjacent to the first support 146. As illustrated in FIGS. 5 to 7, the guiding groove 144 may be located adjacent to the first support 146 in the opposite direction to the rotation direction R1. The guiding groove 144 may be formed at the body 141 in a cut shape with a certain width. The guiding groove 144 may be provided to penetrate the body 141 in the needle (ND) insertion direction K, for example, in the Z-axis direction of the drawings. The guiding groove 144 may be provided to pass the guiding member 155 (which will be described below) therethrough in a second state where the needle holder 140 is rotated. That is, in the second state, the guiding member 155 may be inserted into the guiding groove 144, and in this case, the needle holder 140 may be slid by the spring 130 along the needle (ND) insertion direction K.

The first support 146 may include a support groove 146a formed in the shape of a groove having a certain depth in the Z-axis direction on the surface of the body 141 facing the insertion direction K. The support groove 146a may be connected to the guiding groove 144, and a support stopper 146b may be located between the support groove 146a and the guiding groove 144. The support stopper 146b may have the shape of a protrusion protruding in a direction opposite to the direction in which the support groove 146a is formed. The guiding member described below may be supported at the support groove 146a in the first state, and when the needle holder 140 is transformed from the first state to the second state, that is, when the needle holder 140 rotates along the rotation direction R1, the support stopper 146b may provide a certain degree of resistance to the rotation. Thus, when the user rotates the button 120 with a force greater than the resistance, the needle holder 140 may rotate along the rotation direction R1.

Figure 8:
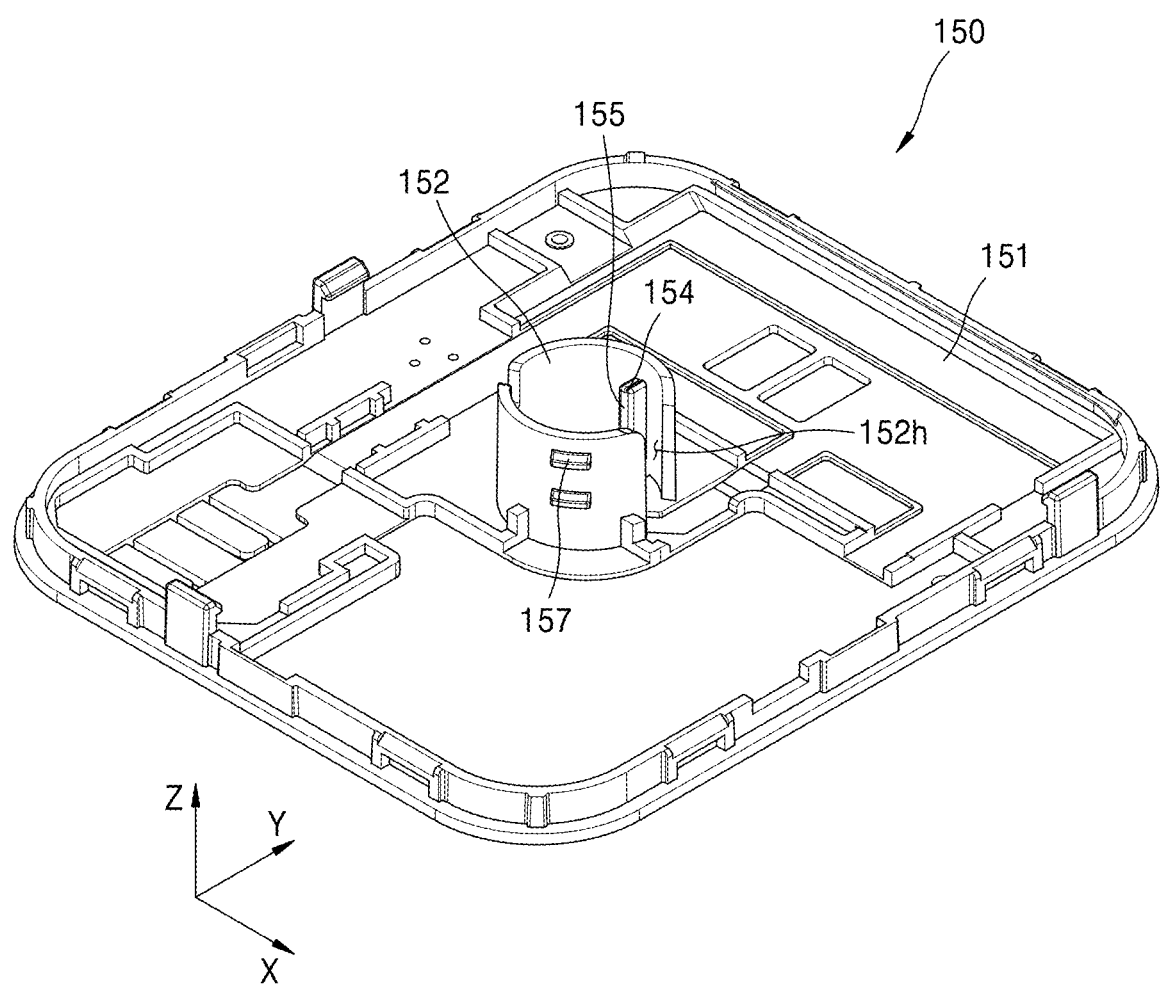
FIG. 8 is a perspective view of a second casing according to an embodiment.
Figure 9:
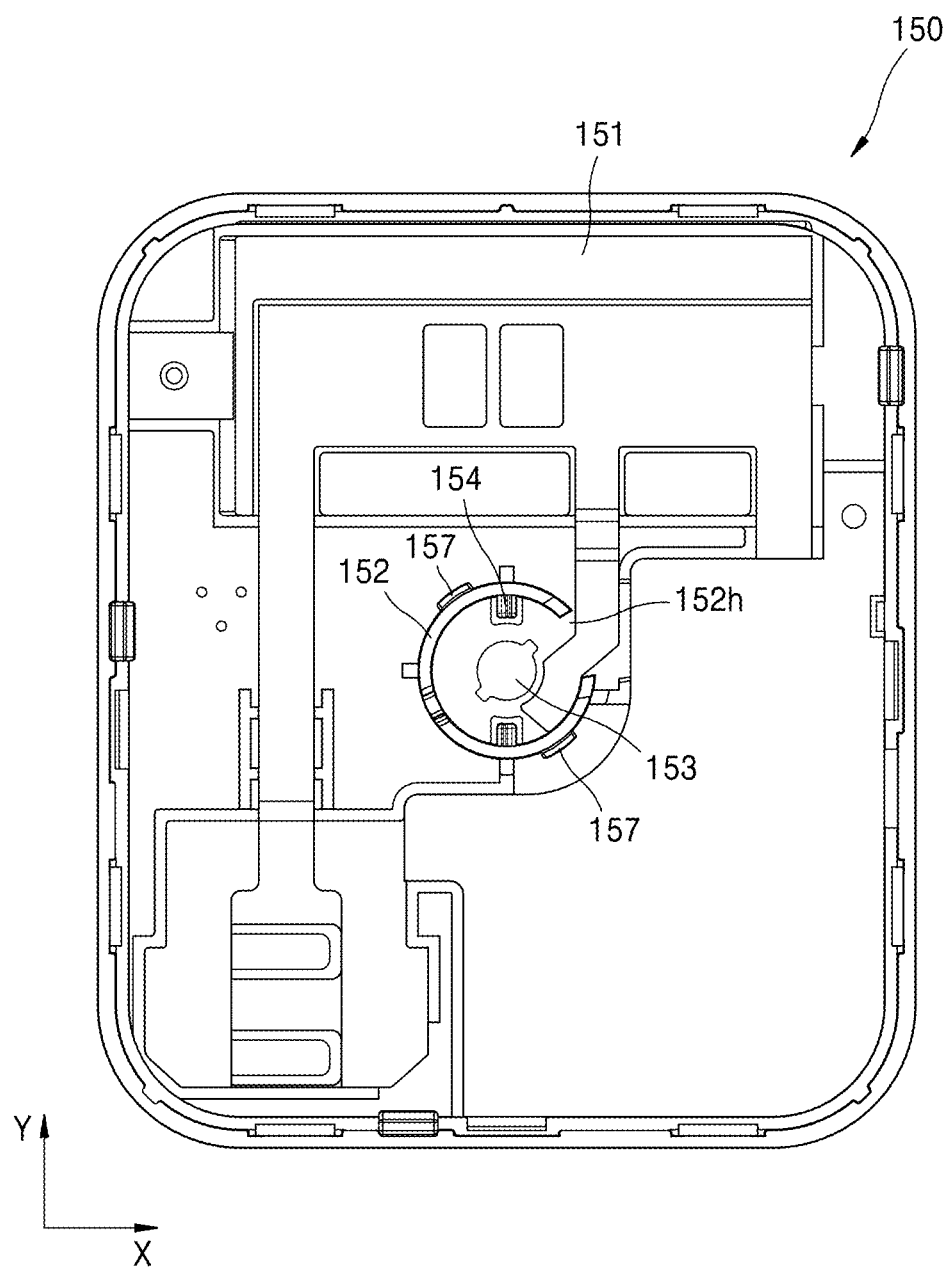
FIG. 9 is a plan view of the second casing illustrated in FIG. 8.
Figure 10:
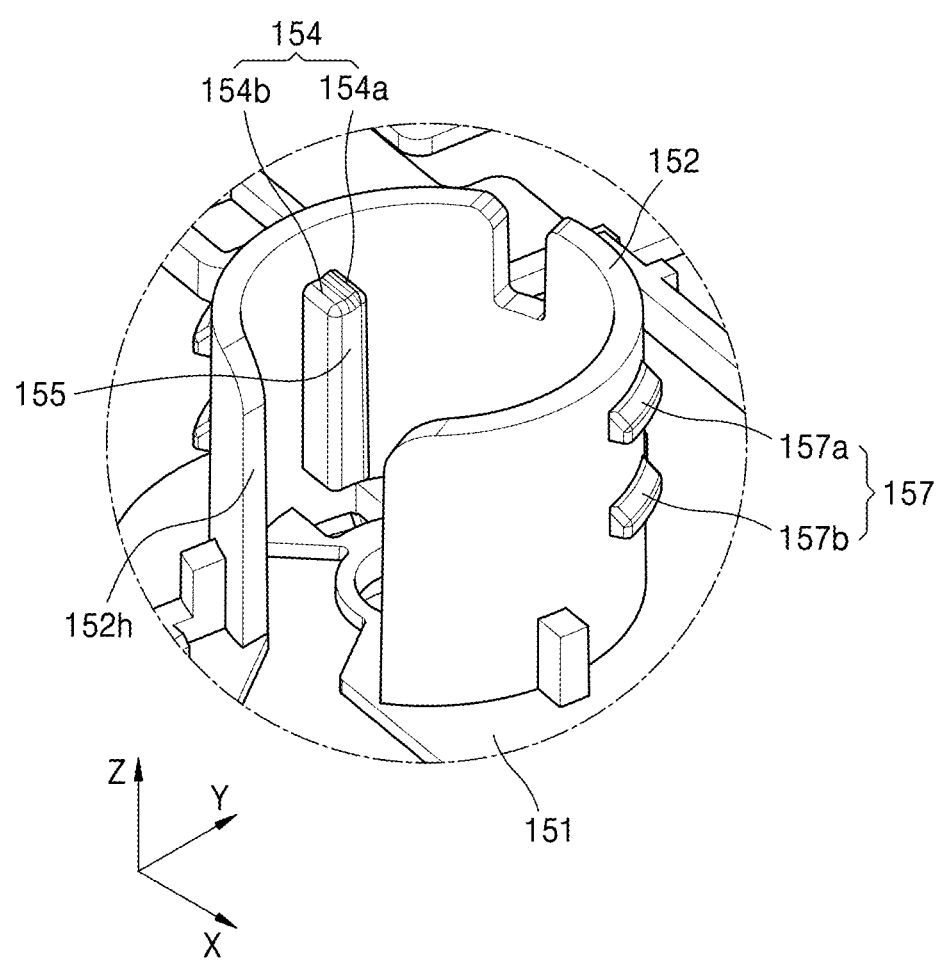
FIG. 10 is a partial perspective view illustrating a portion of the second casing illustrated in FIG. 8.

FIGS. 8 and 9 are respectively a perspective view and a plan view of the second casing 150 according to an embodiment, and FIG. 10 is a partial perspective view illustrating a portion of the second casing 150.

The second casing 150 coupled to the first casing 110 may include a base 151. The base 151 may be a portion of the second casing 150. The base 151 may be formed separately from the second casing 150 and coupled to the bottom of the second casing 150.

A needle through-hole 153 may be formed at a substantially central portion of the base 151 to pass the needle ND therethrough.

A substantially cylindrical guide wall 152 may be formed around the needle through-hole 153. The guide wall 152 may be provided to protrude in the Z-axis direction from the base 151 toward the first casing 110.

As illustrated in FIG. 9, a planar outer diameter of the guide wall 152 may be smaller than an inner diameter of the side surface 123 of the button 120. Accordingly, when the button 120 is pressed, the side surface 123 of the button 120 may be located outside the guide wall 152 and thus the button 120 may slide linearly along the guide wall 152 toward the needle holder 140, that is, along the needle insertion direction K.

As illustrated in FIGS. 8 and 10, a portion of the guide wall 152 may have formed therein a cut groove 152h cut from the base 151 to the opposite end thereof. The connector CN of the needle holder 140 may pass through the cut groove 152h.

A guiding member 155 may be provided on an inner surface of the guide wall 152. The guiding member 155 may be formed to extend in the needle insertion direction K, for example, along the Z-axis direction in FIG. 8, and may be formed in a rail shape. The guiding member 155 may be inserted into the guiding groove 144 in the second state described above, and the needle holder 140 may be slid in the insertion direction K along the guiding member 155.

A second support 154 provided to support the first support 146 in the first state described above may be formed at one end of the guiding member 155, that is, at the end of the guiding member 155 facing the first casing 110. As illustrated in FIG. 10, the second support 154 may include a first support portion 154a and a second support portion 154b. The first support portion 154a and the second support portion 154b may be connected to each other. The first support portion 154a may be located downstream with respect to the rotation direction of the needle holder 140, and the second support portion 154b may be located upstream with respect to the rotation direction of the needle holder 140. In this case, since the first support portion 154a is located more adjacent to the button 120 than the second support portion 154b, when the needle holder 140 rotates along the rotation direction R1, a certain degree of resistance may be provided to the rotation. Thus, when the user rotates the button 120 with a force greater than the resistance, the needle holder 140 may rotate along the rotation direction R1.

A stopper 157 may be formed on an outer surface of the guide wall 152. The stopper 157 may be a protrusion protruding in the X-axis direction from the outer surface of the guide wall 152. As illustrated in FIG. 10, the stopper 157 may extend in the X-Y plane direction along an outer circumferential surface of the guide wall 152.

The stopper 157 may be provided to control the sliding of the button 120 in the Z-axis direction and may include a first stopper 157a and a second stopper 157b that are spaced apart in parallel along the Z-axis direction. The first stopper 157a and the second stopper 157b may be inserted into the fastening opening 127 of the button 120 illustrated in FIGS. 3 and 4, and the fastening rod 123a may be caught by the first stopper 157a and the second stopper 157b to prevent the button 120 from being detached in the direction opposite to the insertion direction K. The first stopper 157a may be fastened to the fastening opening 127 in a state before the button 120 is pressed, and the second stopper 157b may be fastened to the fastening opening 127 in a state where the button 120 is pressed.

In the liquid medicine injection device 100 according to an embodiment configured as described above, when the user presses the button 120 in a state where the outer surface of the second casing 150 is located at a region where the user will use the liquid medicine injection device 100, the button 120 and the needle holder 140 may be coupled to each other, and when the user rotates the button 120, the needle holder 140 may be slid in the needle (ND) insertion direction K by the elasticity of the spring 130 to instantly insert the needle ND. In this case, the spring 130 may be sufficiently compressed according to the pressing of the button 120, and the effect of the instant insertion of the needle ND by the elasticity of the spring 130 may be increased. The instant insertion of the needle ND may minimize the pain and fear of the patient.

Figure 11A:
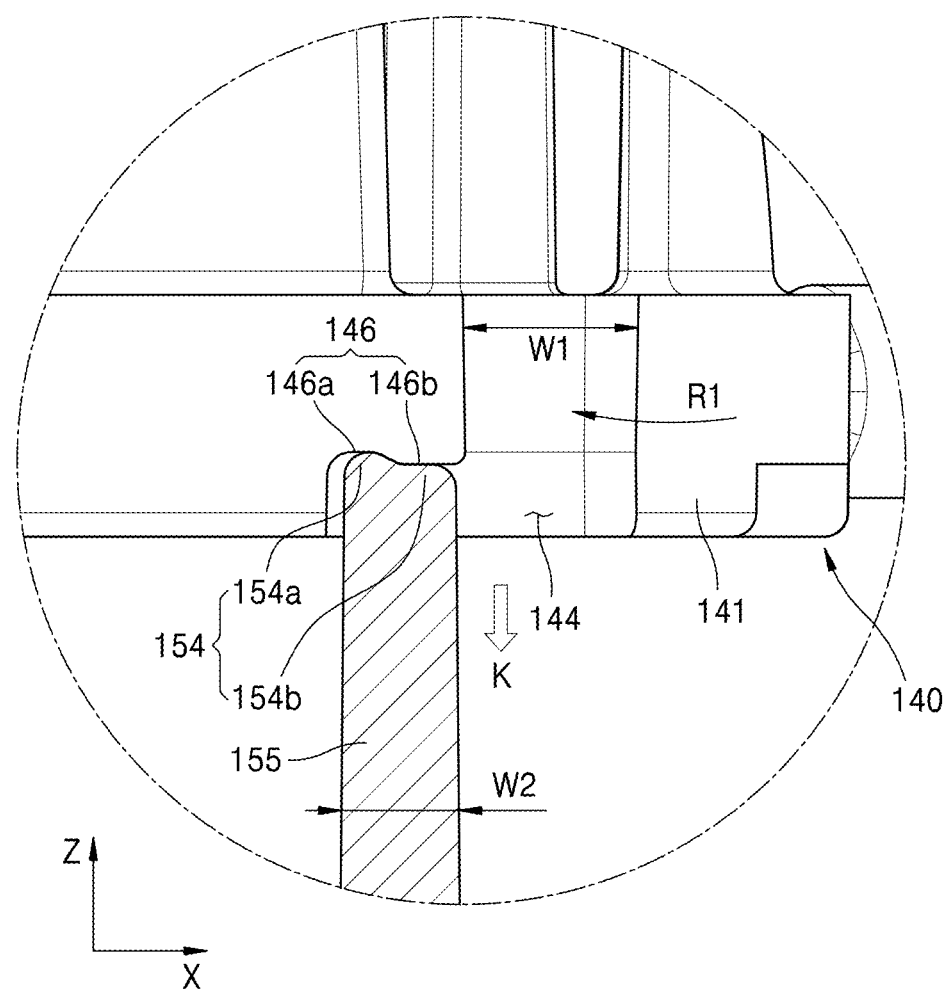
FIGS. 11A and 11B are diagrams illustrating the states of a needle holder and a guiding member in a first state and a second state, respectively.

According to an embodiment, for example, as illustrated in FIG. 11A, in a first state where the needle holder 140 is not rotated, the needle holder 140 may be spaced apart from the base 151 of the second casing 150. In this state, the needle ND may not be inserted into the body of the patient. In the first state, the first support 146 of the needle holder 140 may contact and support the second support 154 of the guiding member 155. In this case, according to an embodiment, the first support 146 and the second support 154 may engage with each other and thus the support groove 146a and the first support portion 154a may contact each other and the support stopper 146b and the second support portion 154b may contact each other. Thus, in the first state, the needle holder 140 may be more stably supported by the end of the guiding member 155.

When the user rotates the button 120 and thus the needle holder 140 rotates along the rotation direction R1, the support stopper 146b and the first support portion 154a may move relatively in directions intersecting each other and thus a resistance to the rotation may be provided to the needle holder 140. When the user rotates the button 120 with a force exceeding the resistance and thus a rotational force exceeding the resistance is applied to the needle holder 140, the support stopper 146b may pass over the first support portion 154a and thus the guiding member 155 may enter the guiding groove 144.

The guiding groove 144 and the guiding member 155 may have a first width W1 and a second width W2 in the X-axis direction, respectively. The first width W1 may exceed the second width W2 such that the guiding member 155 may be smoothly inserted into the guiding groove 144.

Figure 11B:
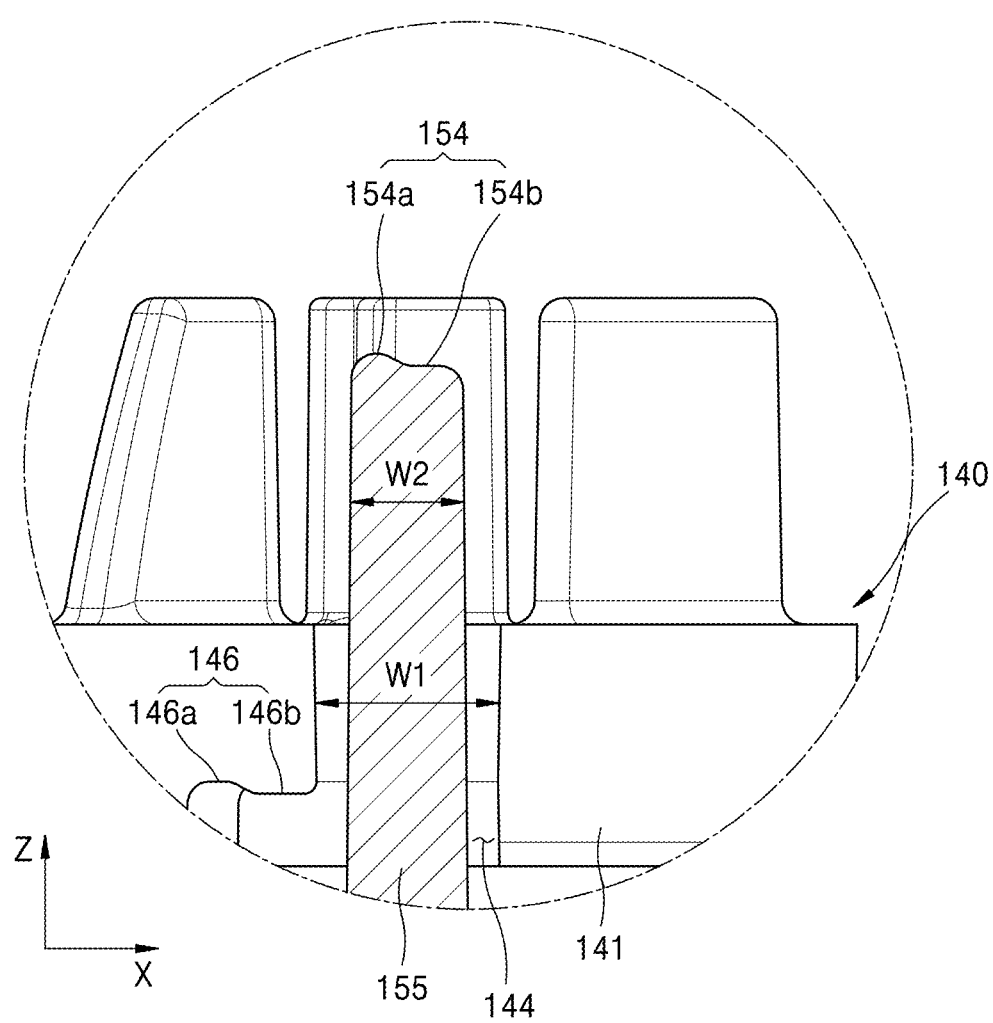

Thus, as illustrated in FIG. 11B, when the user rotates the button 120 and thus it becomes a second state where the needle holder 140 is completely rotated, the needle holder 140 may be driven toward the base 151 of the second casing 150 by being slid along the guiding member 155 in a state where the guiding member 155 is inserted into the guiding groove 144 and thus the needle ND may inserted into the body of the patient.

According to the present disclosure, since the compressed force of the spring may be instantly emitted to drive the needle holder toward the base, the needle coupled to the needle holder may be instantly inserted into the body of the patient.

In order to provide a resistance to the rotation of the needle holder and induce the user to apply a rotational force exceeding the resistance to the button, the liquid medicine injection device according to the above embodiment may include the first support 146 of the needle holder and the second support 154 of the guiding member 155; however, the present disclosure is not limited thereto. That is, it may not be necessary to provide a resistance to the rotation of the needle holder, and the present disclosure may also include any other configuration in which the needle holder may be instantly inserted into the body of the patient by rapidly sliding the needle holder by using the elastic force of the spring according to the rotation of the needle holder by the user.

A liquid medicine injection device according to another embodiment may further include a needle cover assembly in order to protect a needle before the user uses the needle.

Figure 12:
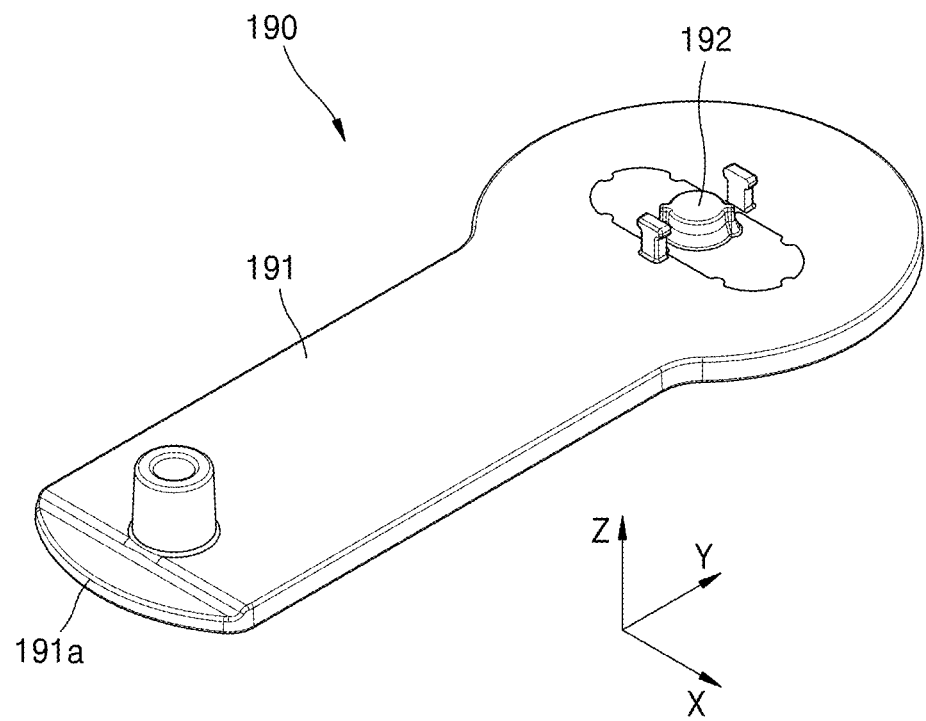
FIG. 12 is a perspective view of a needle cover assembly according to an embodiment.

FIG. 12 is a perspective view of the needle cover assembly 190 according to an embodiment.

The needle cover assembly 190 may include a cover plate 191. The cover plate 191 may be provided as a flat plate and one end thereof may be formed as a handle 191a and thus the user may use the handle 191a to detach the needle cover assembly 190 from the casing.

The needle cover assembly 190 may include a needle cover 192. The needle cover 192 may be inserted into the needle through-hole 153 provided at the base 151 of the second casing 150. Although not illustrated, the needle cover 192 may include a closed space, and a tip portion of the needle may be inserted into the closed space. The closed space may include a portion formed of a material through which air passes but liquid does not pass, or a portion capable of varying in volume, thus preventing the liquid medicine from being discharged outside in a priming operation of the user to remove the air from the inside of the needle and/or the inside of the tube.

Although the present disclosure has been described with reference to the embodiments illustrated in the drawings, this is merely an example and those of ordinary skill in the art will understand that various modifications and other equivalent embodiments may be derived therefrom. Thus, the spirit and scope of the present disclosure should be defined by the appended claims.

INDUSTRIAL APPLICABILITY

The embodiments of the present disclosure may be applied to various liquid medicine injection devices, such as insulin injection devices, used to inject liquid medicines into the bodies of patients.

The invention claimed is:

1. A liquid medicine injection device comprising:
   a casing;
   a button exposed outside the casing;
   a needle holder located in the casing and coupled to a needle, wherein the needle holder is configured to rotate by actuation of the button;
   a spring located in the casing and interposed between the button and the needle holder,
   wherein the button and the needle holder are rotationally coupled to each other such that rotating the button causes a corresponding rotation of the needle holder; and
   a guiding member located in the casing to support the needle holder wherein the needle holder comprises: a first support supported by the guiding member in a first state; and a guiding groove provided to be adjacent to the first support and to pass the guiding member therethrough in a second state where the needle holder is rotated from the first state.

2. The liquid medicine injection device of claim 1, wherein the first support comprises:
   a support groove formed at a surface facing an insertion direction of the needle and connected to the guiding groove; and
   a support stopper located between the support groove and the guiding groove, the support stopper configured to provide resistance to the corresponding rotation of the needle holder.

3. The liquid medicine injection device of claim 1, wherein the guiding member comprises a second support provided to support the first support in the first state.

4. The liquid medicine injection device of claim 3, wherein the second support comprises a first support portion located downstream with respect to a rotation direction of the needle holder and a second support portion located upstream with respect to the rotation direction of the needle holder, and wherein the first support portion is located more adjacent to the button than the second support portion.

5. The liquid medicine injection device of claim 1, wherein the button is provided to slide in a direction facing the needle holder, and
   the liquid medicine injection device further comprises a stopper located adjacent to the guiding member and configured to control the sliding of the button.

6. A liquid medicine injection device comprising:
   a casing comprising a base;
   a button exposed outside the casing;
   a needle holder located in the casing;
   a spring located in the casing and interposed between the button and the needle holder and a guiding member located in the casing to support the needle holder, wherein the needle holder comprises: a first support supported by the guiding member in the first state; and a guiding groove configured to be adjacent to the first support and to pass the guiding member therethrough in the second state where the needle holder is rotated from the first state,
   wherein the button comprises a first coupling portion protruding toward the needle holder,
   wherein the needle holder comprises a second coupling portion provided to couple to the first coupling portion,
   wherein the button and the needle holder are rotationally coupled to each other such that rotating the button causes a corresponding rotation of the needle holder,
   wherein the needle holder is configured to be spaced apart from the base of the casing in a first state, and wherein the needle holder is configured to be driven toward the base by an elasticity of the spring while being transformed into a second state in which the needle holder is rotated with respect to the first state.

7. The liquid medicine injection device of claim 6, wherein the guiding member is configured to support the needle holder to be spaced apart from the base in the first state and to guide the needle holder in the second state.

8. The liquid medicine injection device of claim 6, wherein the guiding member comprises a second support provided to support the first support in the first state.

\* \* \* \* \*

UNITED STATES PATENT AND TRADEMARK OFFICE
CERTIFICATE OF CORRECTION

PATENT NO. : 10,786,622 B2
APPLICATION NO. : 16/080652
DATED : September 29, 2020
INVENTOR(S) : Seung Ha Kim et al.

Page 1 of 1

It is certified that error appears in the above-identified patent and that said Letters Patent is hereby corrected as shown below:

In the Specification

In Column 1, Line 27, after "device." insert --SUMMARY OF CERTAIN INVENTIVE ASPECTS--.

In Column 1, Line 30, below "needle." delete "SOLUTION TO PROBLEM".

In Column 5, Line 47, delete "below" and insert --below)--.

In Column 6, Line 16, delete "120," and insert --120.--.

Signed and Sealed this
First Day of December, 2020

Andrei Iancu
*Director of the United States Patent and Trademark Office*